United States Patent [19]

Cox

[11] Patent Number: Plant 6,105

[45] Date of Patent: Feb. 16, 1988

[54] COX'S MIRACLE BERRY

[76] Inventor: Mason E. Cox, Box 262, Pineville, W. Va. 24874

[21] Appl. No.: 403

[22] Filed: Jan. 5, 1987

[51] Int. Cl.[4] ..... A01H 5/03

[52] U.S. Cl. ..... Plt./46

[58] Field of Search ..... Plt. 46

*Primary Examiner*—Robert E. Bagwill

*Attorney, Agent, or Firm*—George J. Neilan

[57] ABSTRACT

A new and distinct variety of blackberry plant which exhibits an absence of thorns, and two crops per season with sprouts of the second crop appearing about the time that the berries of the first crop begin to ripen. The plants have sturdy canes with generally round berries that ripen over an extended period of time.

2 Drawing Figures

SUMMARY OF THE INVENTION

This invention relates to a new and distinct variety of a thornless blackberry plant that was discovered by me on my farm on Pinnacle Road, Pineville, W. Va., in a cultivated area. The plant has been reproduced asexually by burying tips of the canes.

My discovery has inter alia, the following characteristics:

1. an absence of thorns;
2. two crops per season with sprouts of the second crop appearing about the time that the berries of the first crop begin to ripen;
3. the plants grow in the form of low, wide bushes that are erect or semi-erect;
4. stout canes support clusters of large, generally round berries; and
5. the berries which are glossy black in color ripen over an extended period of time.

BRIEF DESCRIPTION OF THE DRAWINGS

The accompanying drawings are color photographs showing typical specimens of the new variety in color as nearly true as is reasonably possible to make in a color illustration of this character.

The close-up view shows the configuration and clustering of ripening berries, only several of the berries having matured into glossy black berries.

The other view shows the low, spreading configuration of a typical plant.

DETAILED DESCRIPTION OF THE NEW VARIETY

The following description was made from plants growing at Pineville, W. Va.

Where sizes, colors and other characteristics are given, it will be understood that such characteristics are approximations of average values.

Growing Season: The plant has two crops per season, with the second crop beginning about the time that the fruit of the first crop begins to ripen. In a typical year, the first bloom or flowering of the first crop began to appear on May 25, with the flowers being white. The flowers last about 3–4 weeks. About July 10, the berries begin to ripen, turning from red to a glossy black, as illustrated in the drawing. About the same time, the second crop begins to shoot large sprouts down low on the canes. Shooting straight up, the longer sprouts grow as high as the rest of the bush. Some of the longer sprouts fork about midpoint and have as many as four forks with four large clumps of berries on each fork. Smaller sprouts tend to grow out to the sides.

The flowers of the second crop also last about 3–4 weeks. The fruiting for the second crop follows the same pattern as for the first crop. Thus, the second crop's berries began ripening about September 1, and continued ripening for 3–4 weeks.

Plant form: The plant grows in the form of low, wide bushes having a width of about 10 feet. The cane grows to 3 to 4 feet high, and the limbs grow up from the cane giving the bush a height of about 5 feet. The canes are stout having a circumference at their widest of 4–5 inches. The plant may be characterized as erect to semi-erect. The canes initially have a dark green color and as they grow older change to a maroon-like color. The roots are white and extend straight down, providing good drought tolerance.

Foliage: The leaves are dark green and are similar to the wild blackberry leaf. The leaves are compound and generally have five leaflets.

Fruit: The berries are generally round and generally have a length of 1 to 1¼ inches. The berries are found in clumps. The ripe berries have a glossy black color. The seeds are medium-large.

Resistance: The plants have withstood 0 degrees F. with the wind blowing, without cover and have not been damaged. Since the plants are late blooming; the danger of frost is minimized. No herbicides have been used on the plants and they appear relatively disease resistant.

The new variety described herein is being named Cox's Miracle Berry.

I claim:

1. A new and distinct variety of blackberry, substantially as shown and described, characterized by being thornless, round berries, and two crops per season.

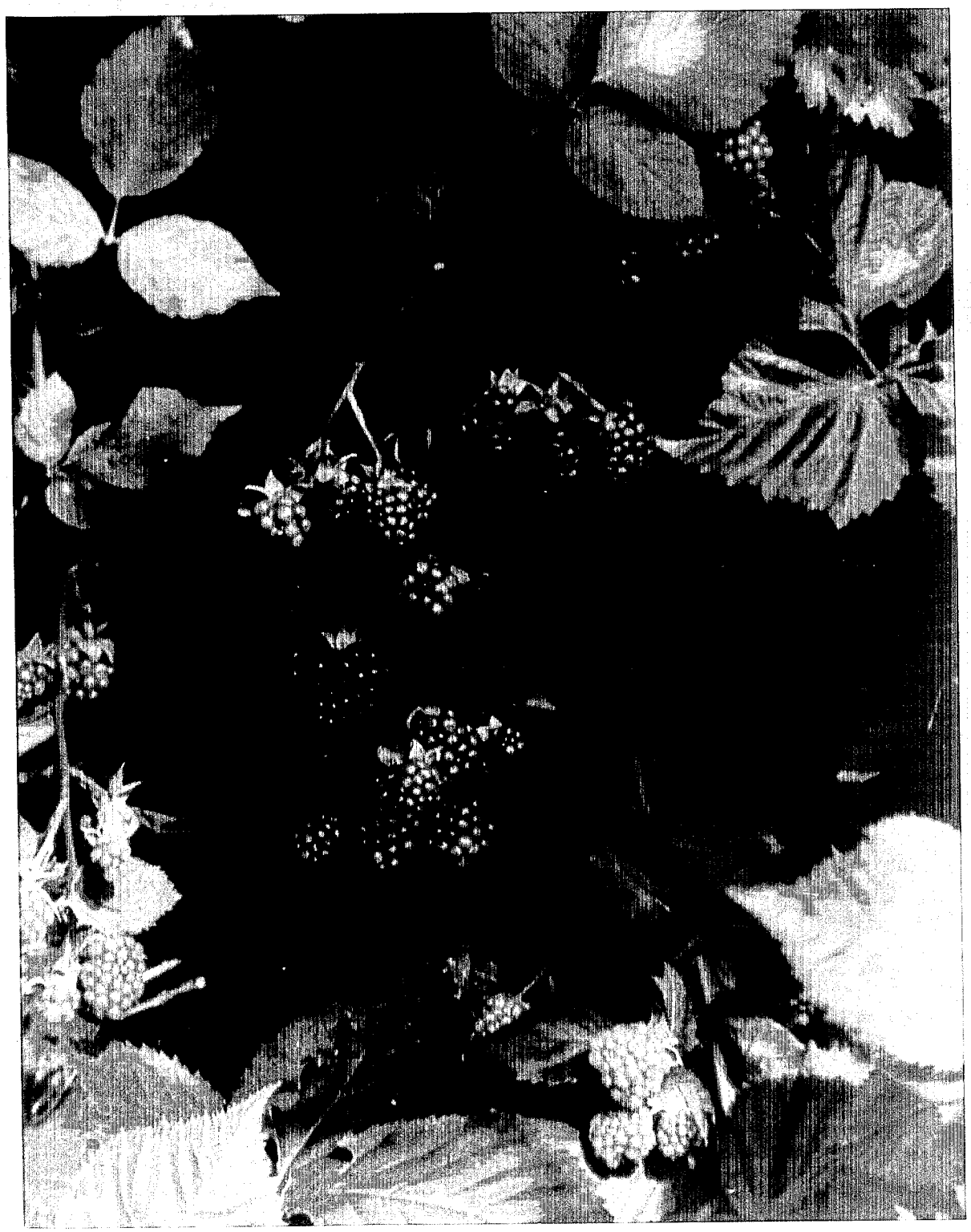

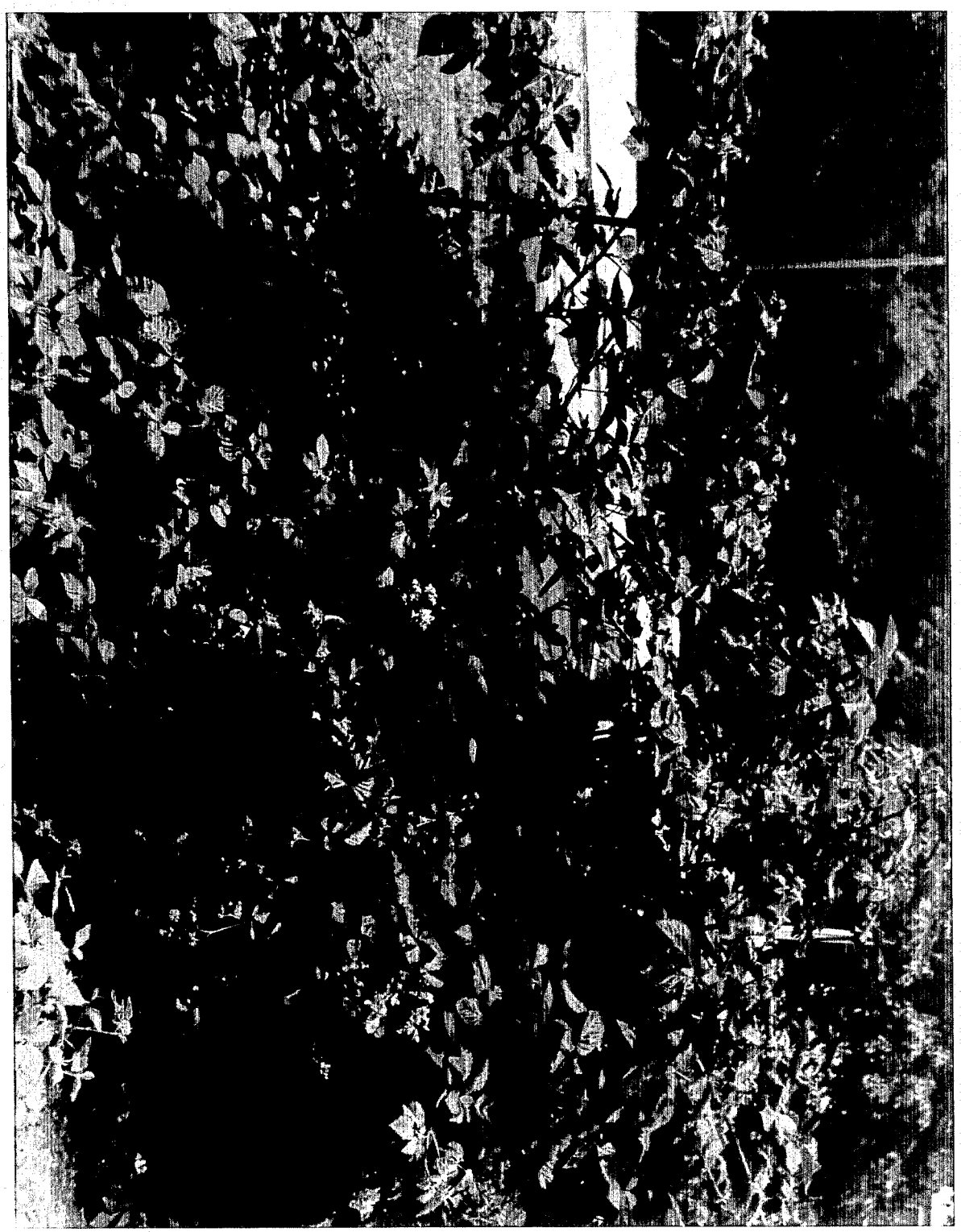

* * * * *